United States Patent
Breault et al.

(10) Patent No.: US 11,197,703 B2
(45) Date of Patent: Dec. 14, 2021

(54) FIXATION ARTICLE FOR AN IMPLANT

(71) Applicant: Kelyniam Global, Inc., Canton, CT (US)

(72) Inventors: Nicholas Breault, Bloomfield, CT (US); Merwin Schaefer, New Britain, CT (US); Christopher J. Breault, New Britain, CT (US)

(73) Assignee: Kelyniam Global, Inc., Canton, CT (US)

( * ) Notice: Subject to any disclaimer, the term of this patent is extended or adjusted under 35 U.S.C. 154(b) by 757 days.

(21) Appl. No.: 14/577,667

(22) Filed: Dec. 19, 2014

(65) Prior Publication Data

US 2015/0173815 A1   Jun. 25, 2015

Related U.S. Application Data

(60) Provisional application No. 61/918,878, filed on Dec. 20, 2013.

(51) Int. Cl.
  *A61B 17/80*   (2006.01)

(52) U.S. Cl.
  CPC ...... *A61B 17/8061* (2013.01); *A61B 17/8085* (2013.01)

(58) Field of Classification Search
  CPC ..................... A61B 17/80–17/8095; A61F 2/2875–2002/2889
  See application file for complete search history.

(56) References Cited

U.S. PATENT DOCUMENTS

| | | | | |
|---|---|---|---|---|
| 5,201,737 A | * | 4/1993 | Leibinger | A61B 17/688 606/280 |
| 5,372,598 A | * | 12/1994 | Luhr | A61B 17/8085 606/285 |
| 5,383,931 A | * | 1/1995 | Hehli | A61B 17/8061 623/17.18 |
| 5,578,036 A | * | 11/1996 | Stone | A61B 17/688 606/281 |
| 5,743,913 A | * | 4/1998 | Wellisz | A61B 17/8061 606/285 |
| 6,620,165 B2 | * | 9/2003 | Wellisz | A61B 17/688 606/285 |
| 2002/0120268 A1 | * | 8/2002 | Berger | A61B 17/7055 606/300 |
| 2003/0100898 A1 | * | 5/2003 | Wellisz | A61B 17/8061 606/297 |

(Continued)

*Primary Examiner* — Zade Coley
(74) *Attorney, Agent, or Firm* — Reinhart Boerner Van Deuren P.C.

(57) ABSTRACT

A cranial implant and a method for generating and implementing the cranial implant is provided, wherein the cranial implant includes at least one fixation tab. The method includes determining the characteristics of a skull of a patient and an opening in the skull, identifying the desired location of the at least one fixation tab, fabricating the cranial implant based on at least one of a predetermined algorithm and experience of a fabricator in response to at least one of the characteristic of the skull/opening in the skull and the location of the fixation tabs, adjusting the cranial implant to fit within the opening of the skull such the cranial implant is substantially flush with a surface of the skull and securing the cranial implant to the skull using one or more fixation screws.

12 Claims, 19 Drawing Sheets

(56) References Cited

U.S. PATENT DOCUMENTS

| | | | |
|---|---|---|---|
| 2006/0094951 A1* | 5/2006 | Dean | A61F 2/30942 |
| | | | 600/407 |
| 2006/0287654 A1* | 12/2006 | Posnick | A61B 17/688 |
| | | | 606/279 |
| 2012/0010711 A1* | 1/2012 | Antonyshyn | A61F 2/30942 |
| | | | 623/16.11 |
| 2012/0289964 A1* | 11/2012 | Nakaji | A61B 17/8085 |
| | | | 606/80 |
| 2013/0172941 A1* | 7/2013 | Correa de Mendonca | |
| | | | A61B 17/8061 |
| | | | 606/280 |

\* cited by examiner

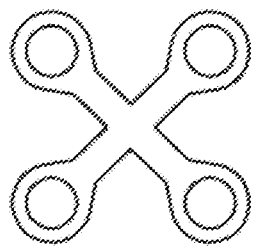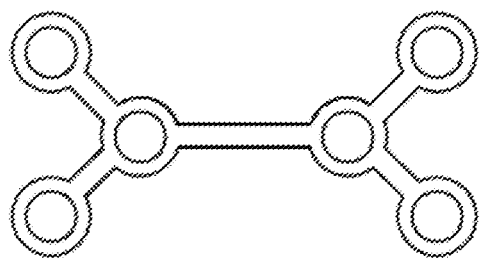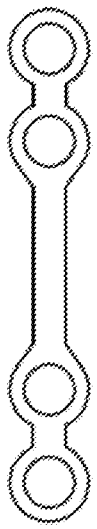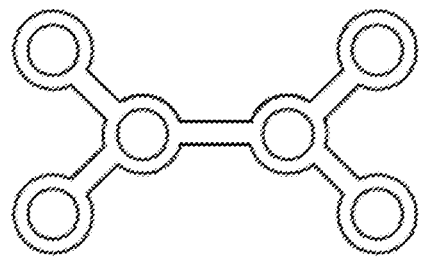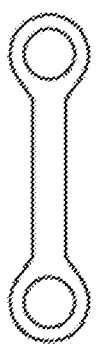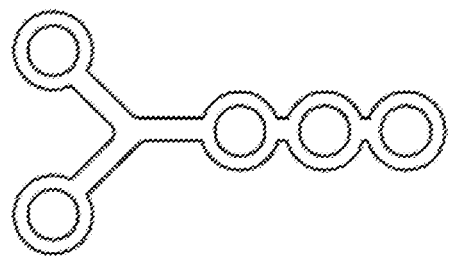
FIG. 1
Prior Art

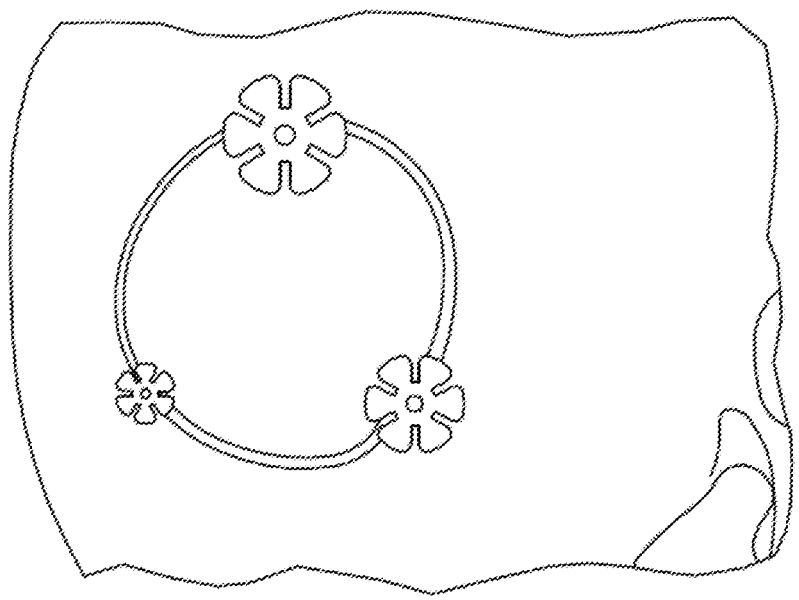
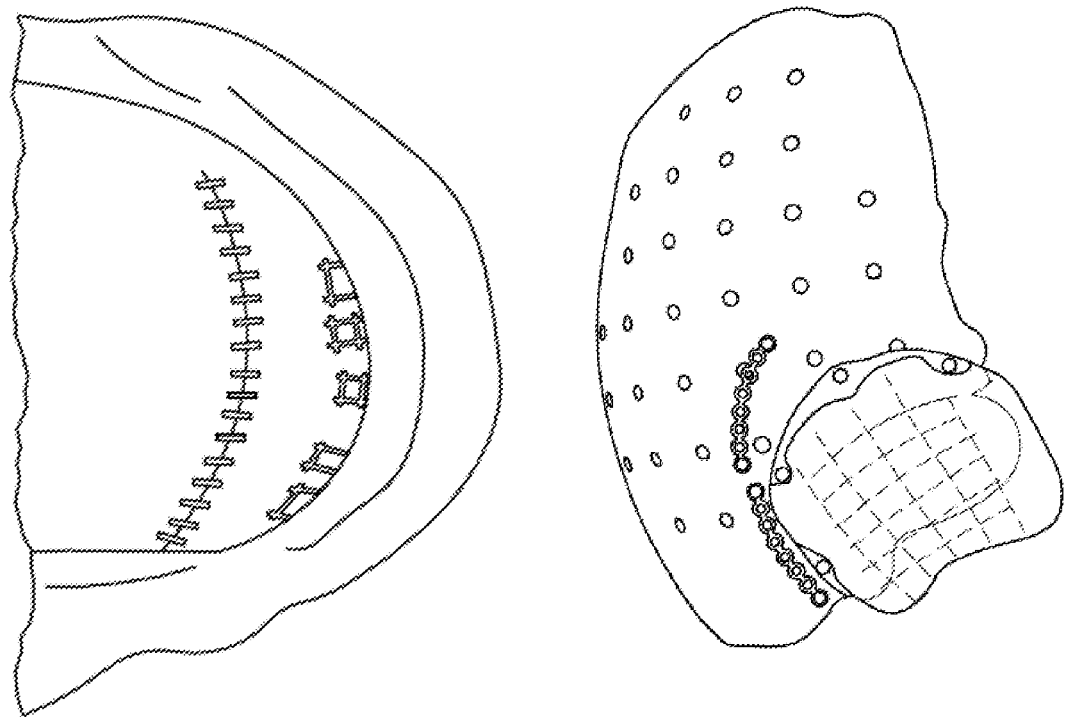
FIG. 4
Prior Art

FIXATION ARTICLE FOR AN IMPLANT

CROSS-REFERENCE TO RELATED APPLICATIONS

This application is related to U.S. Design patent application Ser. No. 29/472,313 and U.S. Provisional Patent Application Ser. No. 61/918,878 and claims the benefit of priority of the filing date of U.S. Provisional Patent Application Ser. No. 61/918,878, filed on Dec. 20, 2013, the contents of both of which are incorporated herein by reference in their entireties.

FIELD OF THE INVENTION

This invention relates generally to an implant and more particularly to a a fixation tab for use with cranial and other biological implants.

BACKGROUND OF THE INVENTION

Cranial implants are well known in the medical field and are used to replace the boney areas of the skull that have been damaged by trauma or that have been removed during brain surgery to either provide access to the brain or to relieve pressure on the brain. Typically a cranial plate is made from a rigid material and is constructed to resemble the shape of the opening in the skull such that the cranial plate fits within the opening in the skull to mimic the bone. The cranial plate is positioned within the opening in the skull such that the edge of the plate rests on the edge of the skull surrounding the opening. The plate is adjusted so that the plate is as flush as possible with the skull to minimize bumps and protrusions under the skin. Fixation tabs are then used to attach the cranial plate to the skull by screwing one end of the tab to the non-damaged, intact part of the skull and screwing the other end of the tab to the cranial plate. Various types of these attachment articles that are currently used are shown in FIG. 1, while FIG. 2 and FIG. 3 illustrate several examples showing how these different fixation articles are used to secure the cranial plates to the skull using fixation screws.

Unfortunately however, the current methods that are used to attach the cranial implants to the skull have several problems associated with them. One problem is that the current cranial plate needs to be "pre-plated" before the implant is placed to ensure that it fits correctly. Although the surgeon typically has a maxillofacial fixation kit which provides different plating options to choose from (See FIG. 3), the available plating options may not be optimal for various reasons. Another problem is that because the plates typically start out as being flat, due to inaccuracies in the contouring process they may not contour correctly to the shape of the skull. This may cause the skull to look deformed and uneven. Still yet another problem is that the plates are typically metallic which creates artifacts in CT Scans and X-rays.

SUMMARY OF THE INVENTION

A cranial implant is provided and includes an implant body, having an implant body edge and at least one fixation tab, wherein the at least one fixation tab includes a tab connecting shaft and a tab anchoring end, wherein the tab anchoring end includes at least one anchor opening.

A method for generating and implementing a cranial implant is provided, wherein the cranial implant includes at least one fixation tab. The method includes determining the characteristics of a skull of a patient and an opening in the skull, identifying the desired location of the at least one fixation tab, fabricating the cranial implant based on at least one of a predetermined algorithm and experience of a fabricator in response to at least one of the characteristic of the skull/opening in the skull and the location of the fixation tabs, adjusting the cranial implant to fit within the opening of the skull such the cranial implant is substantially flush with a surface of the skull and securing the cranial implant to the skull using one or more fixation screws.

BRIEF DESCRIPTION OF THE DRAWINGS

The foregoing and other features and advantages of the present invention will be more fully understood from the following detailed description of illustrative embodiments, taken in conjunction with the accompanying drawings in which like elements are numbered alike:

FIG. 1 illustrates several versions of fixation tabs used to secure cranial implants to a skull, in accordance with the prior art.

FIG. 4 illustrates several top down views of fixation tabs being used to secure cranial implants to a skull, in accordance with the prior art.

DETAILED DESCRIPTION OF THE INVENTION

As disclosed herein with regards to an exemplary embodiment, a cranial implant having one or more attachment articles is provided, where the attachment articles are an integrated part of the implant. The present invention provides a way to more easily affix an implant to the skull (or other body part) in a pre-planned manor to reduce the time the patient spends in surgery, to increase the efficiency of the surgeon and to ensure that the implant and its manor of affixation is optimal.

Figure 2:
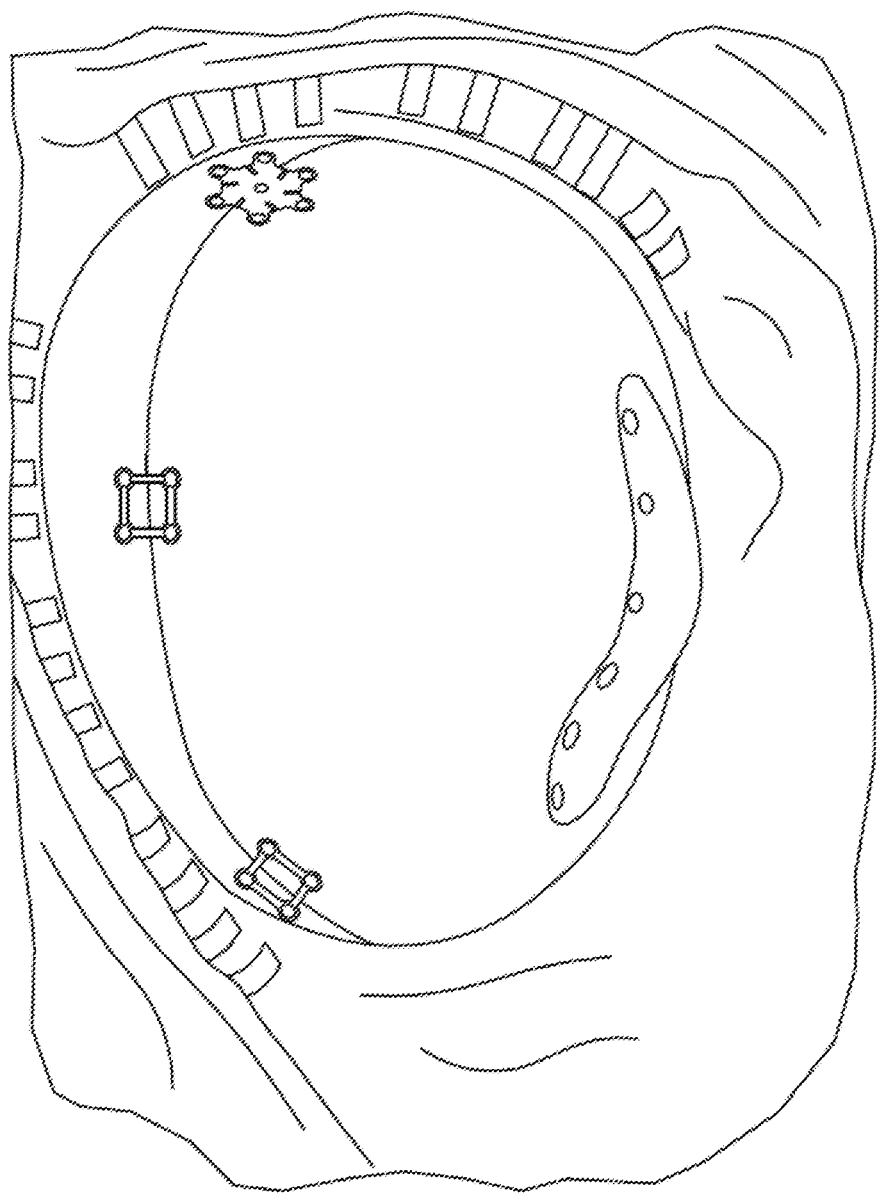
FIG. 2 is a top down view of a cranial implant secured to the skull of a patient using a fixation tab in accordance with the prior art.
Figure 3:
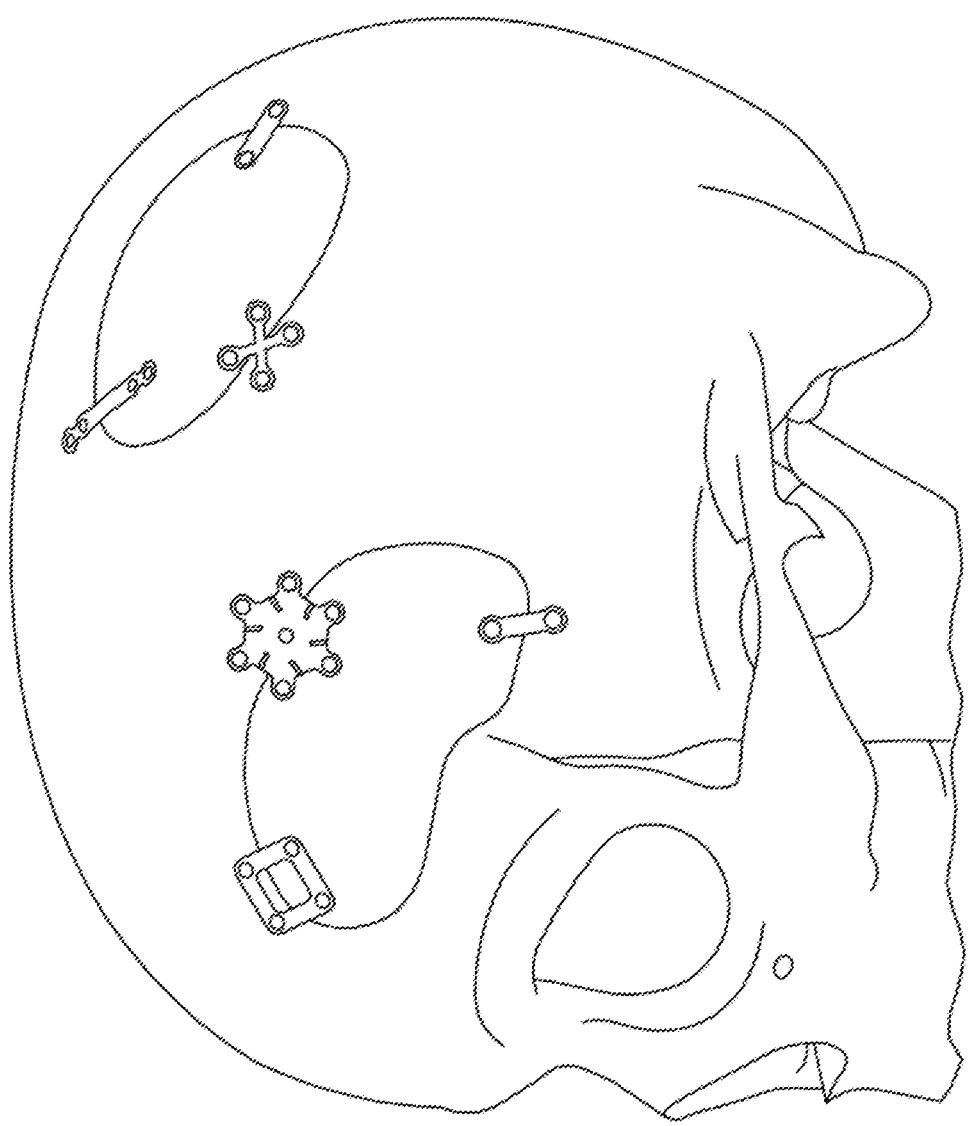
FIG. 3 is a side view of a skull and several versions of fixation tabs used to secure cranial implants to a skull, in accordance with the prior art.
Figure 5:
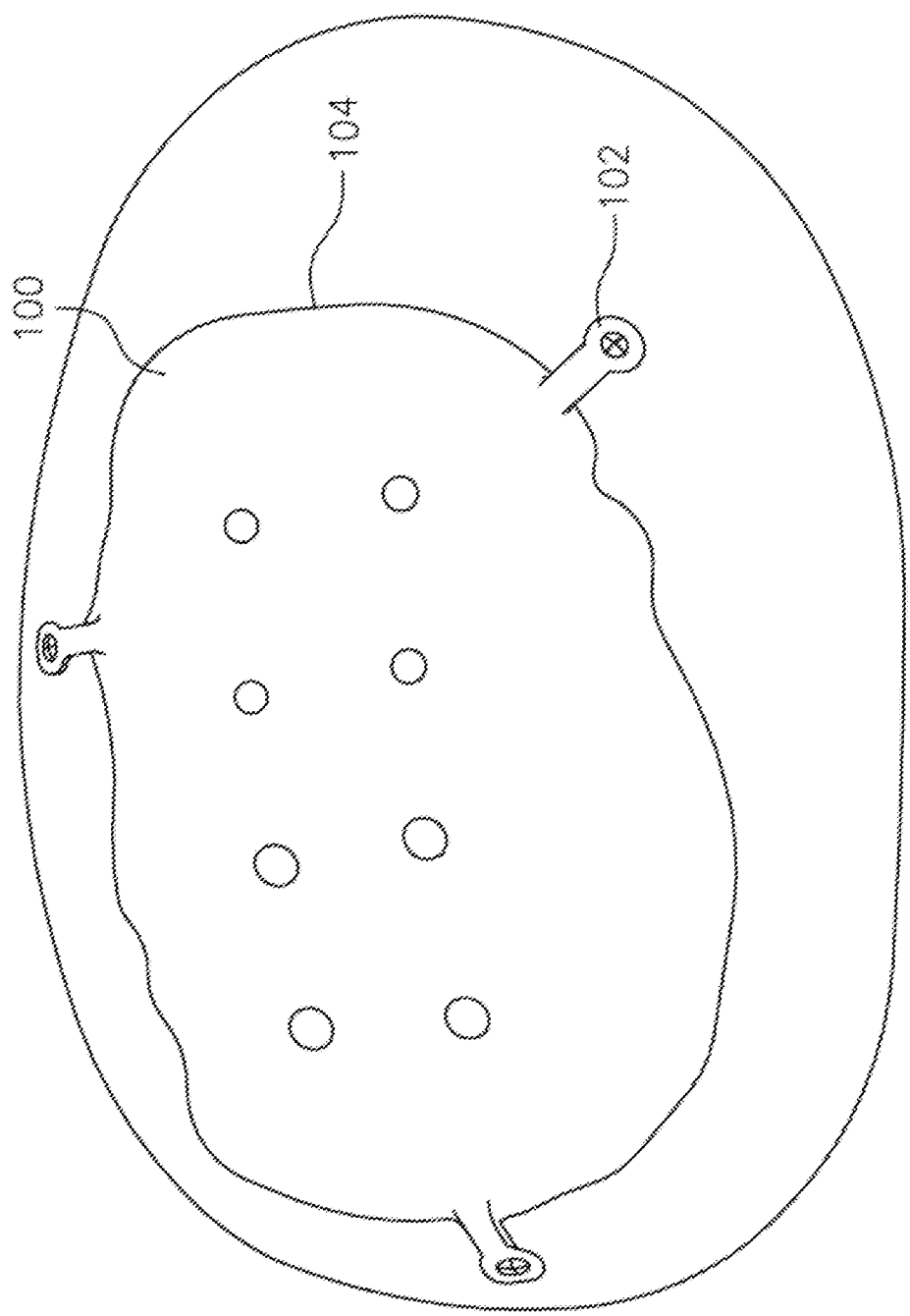
FIG. 5 is top down view of a cranial implant securely associated with a model of a skull via fixation tabs, in accordance with one embodiment of the invention.
Figure 6:
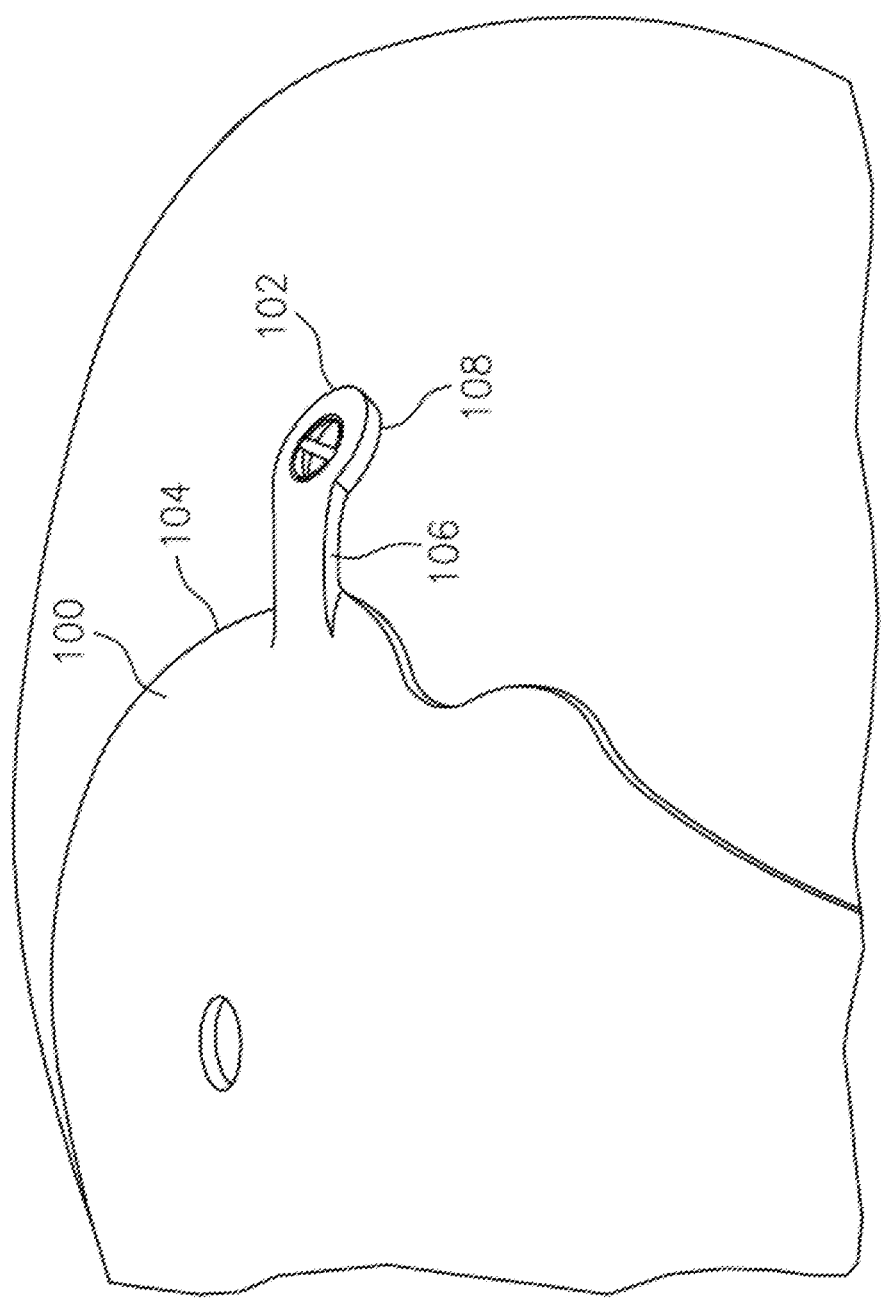
FIG. 6 is side top down view of the cranial implant of FIG. 5 securely associated with a model of a skull via fixation tabs.
Figure 7:
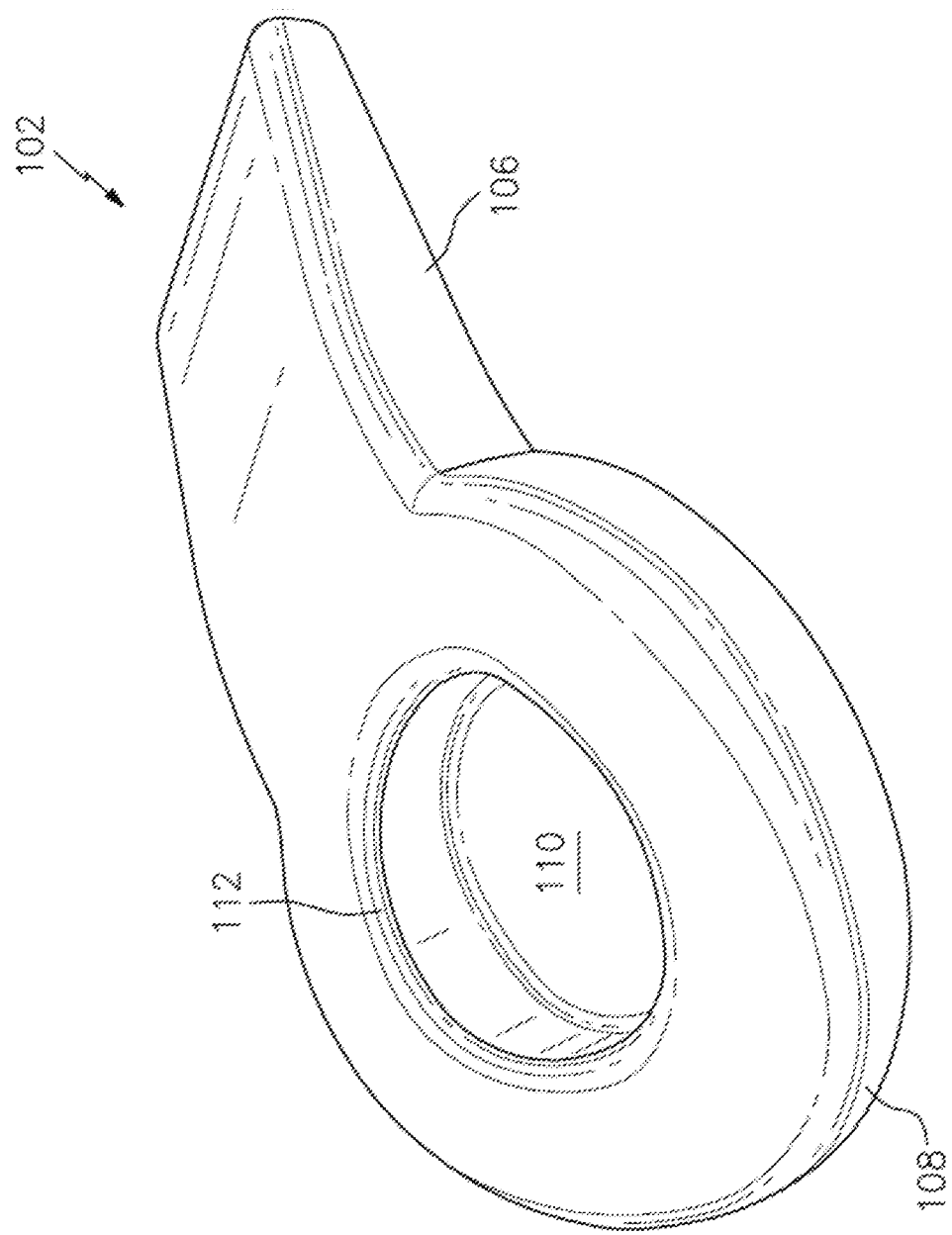
FIG. 7 is a front side perspective view of a fixation tab, in accordance with one embodiment of the invention.

Referring to FIG. 5 and FIG. 6, a cranial implant 100 having a plurality of attachment articles 102 (fixation tabs), an implant center 103 and an implant edge 104 is shown, where the fixation tabs 102 are located proximate the edge 104 of the cranial implant 100, in accordance with one embodiment of the invention. Each of the fixation tabs 102 includes a tab connecting shaft 106 and a tab anchoring end 108, wherein the tab connecting shaft 106 connects the tab anchoring end 108 to the cranial implant 100. It is contemplated that the shape of the cranial implant 100 may be determined by the shape of the opening in the skull of the patient that the plate is designed to cover. However, it should be appreciated that the shape of the cranial implant 100 may be any shape suitable to the desired end purpose.

Referring to FIG. 7, FIG. 8, FIG. 9A and FIG. 10, a fixation tab 102 is shown, in accordance with one embodiment of the invention. As discussed briefly above, the fixation tabs 102 are located proximate the edge 104 of the cranial implant 100 and extend out from the edge 104 of the surface of cranial implant 100. In some embodiments, the fixation tab 102 may extend out from the edge 104 to be substantially parallel to the top surface of the cranial implant 100, while in other embodiments the fixation tab 102 may not be parallel to the top surface of the cranial implant 100 (i.e. may be curved). The fixation tab 102 may be formed to approximate the arcuate (or flat) shape of the skull and thus may be arcuate in shape, where the fixation tab 102 includes a tab focus point $T_{FP}$ (located between the tab connecting shaft 106 and a tab anchoring end 108) about which the tab is curved between 3° and 20° (depending upon the shape of the skull). It should be appreciated that the tab focus point $T_{FP}$ may be located proximate the interface of the tab connecting shaft 106 and the tab anchoring end 108, wherein the tab anchoring end 108 includes at least one anchor opening 110 which includes a counter-sunk/counter-bore portion 112 that is counter-sunk/counter-bore into the tab anchoring end 108.

Figure 8:
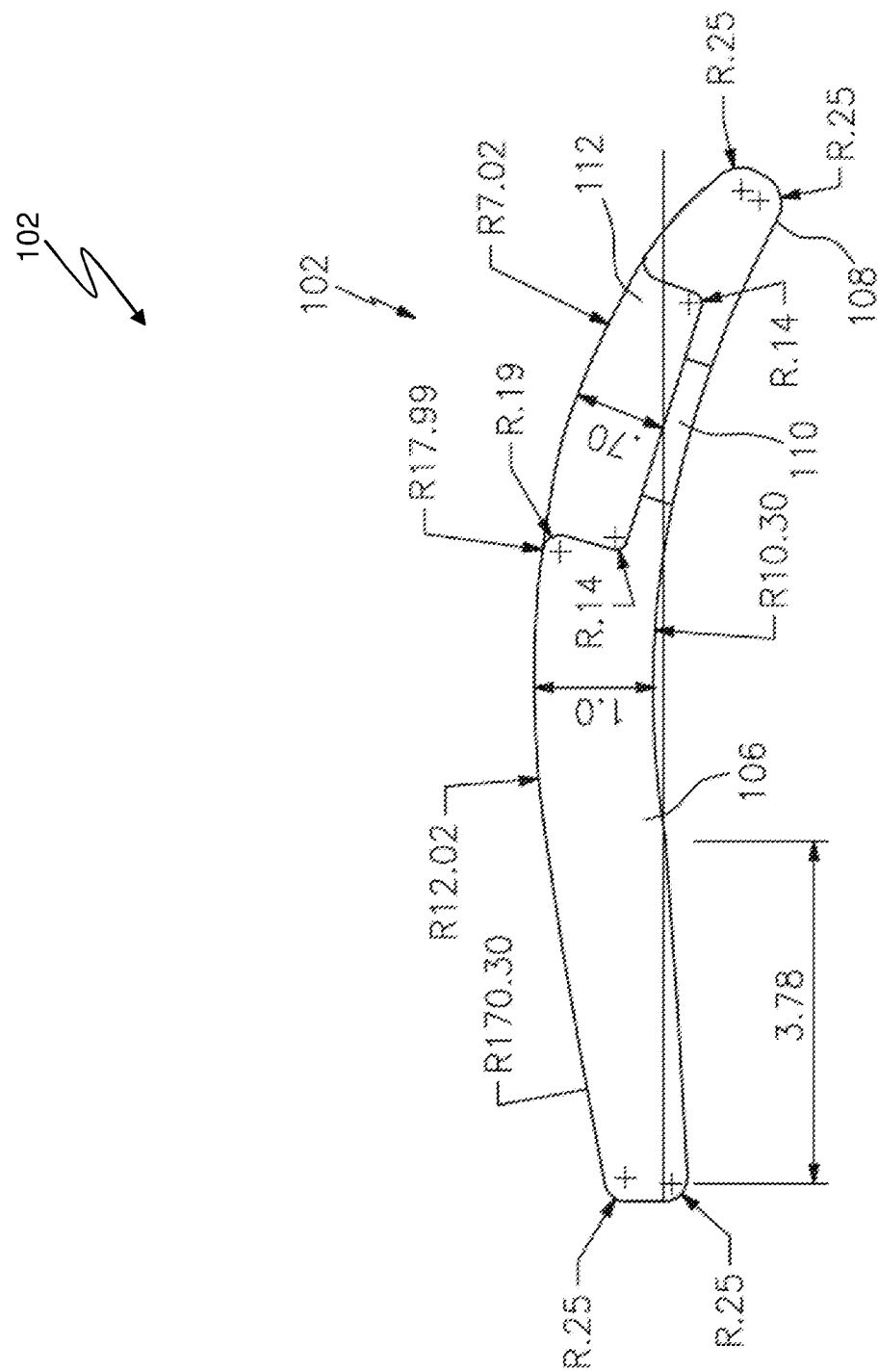
FIG. 8 is a side schematic view of the fixation tab of FIG. 7.

It should be appreciated that the dimensions and radii (radiuses) shown in FIG. 8 and FIG. 9 are express in millimeters and illustrate only one embodiment of the invention. As such, other embodiments are contemplated. As the skull dimensions and radii (radiuses) vary among patients, the cranial implants are adjusted to the size and shape of the skull and cranial implant needed. Thus, it is contemplated that these dimensions and radii (radiuses) will vary in size depending upon the particular application. Additionally, each of the dimensions and radii (radiuses) shown herein with regards to the invention and its contemplated embodiments, may also include an error tolerance of ±20%.

Referring again to FIG. 5 and FIG. 6, once the cranial plate 100 is associated with a skull 116 of a patient to cover the opening in the skull, fixation screws 118 are used to anchor the cranial plate 100 to the skull 116. This may be accomplished by inserting the threaded end of the fixation screw 118 into the at least one anchor opening 110 and rotating the fixation screw 118 until the threaded portion of the fixation screw 118 is located within the skull 116 such that the head of the fixation screw 118 is located within the counter-sunk/counter-bore portion 112 of the tab anchoring end 108. In some embodiments, as the fixation screw 118 is inserted into the counter-sunk/counter-bore portion 112 of the tab anchoring end 108, the at least one anchor opening 100 may be resized (such as by tapping as the screw is being inserted and rotated) by the fixation screw 118 to accommodate the fixation screw 118. It is also contemplated that in other embodiments, the counter-sunk/counter-bore portion 112 of the tab anchoring end 108 may not yet include the at least one anchor opening 110. In this embodiment, the at least one anchor opening 110 may be created by the fixation screw 118 itself or a drill on site.

Figure 9A:
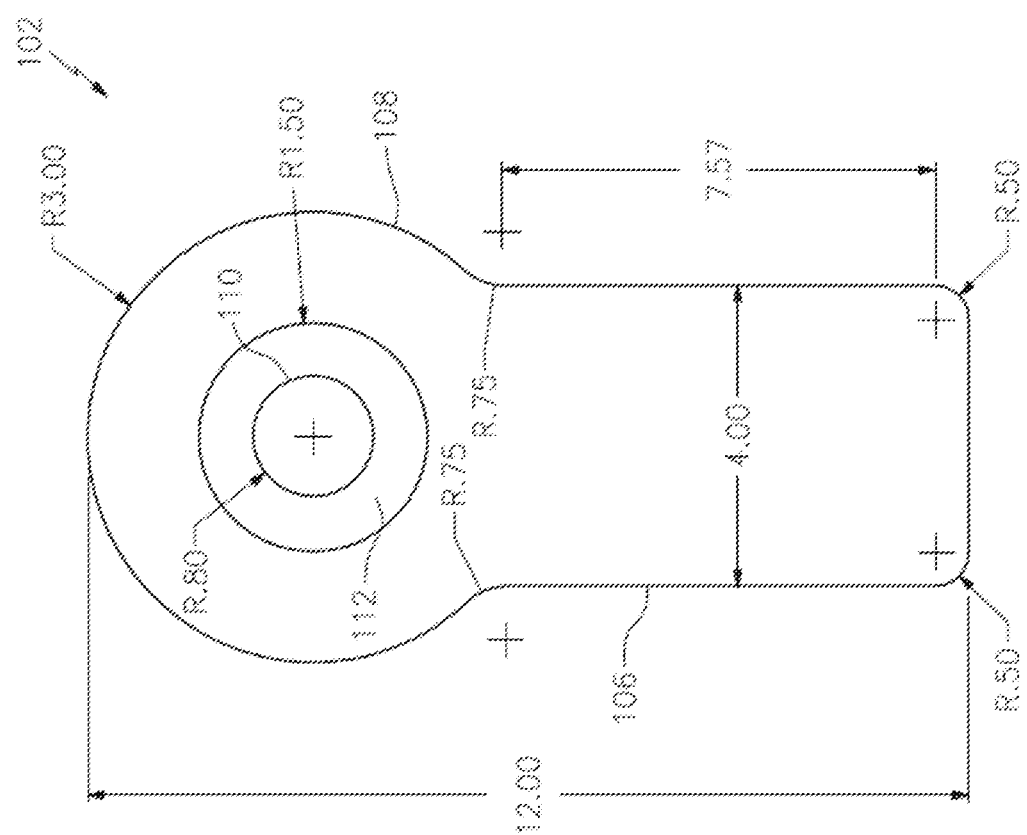
FIG. 9A is a top down schematic view of the fixation tab of FIG. 7.
Figure 9B:
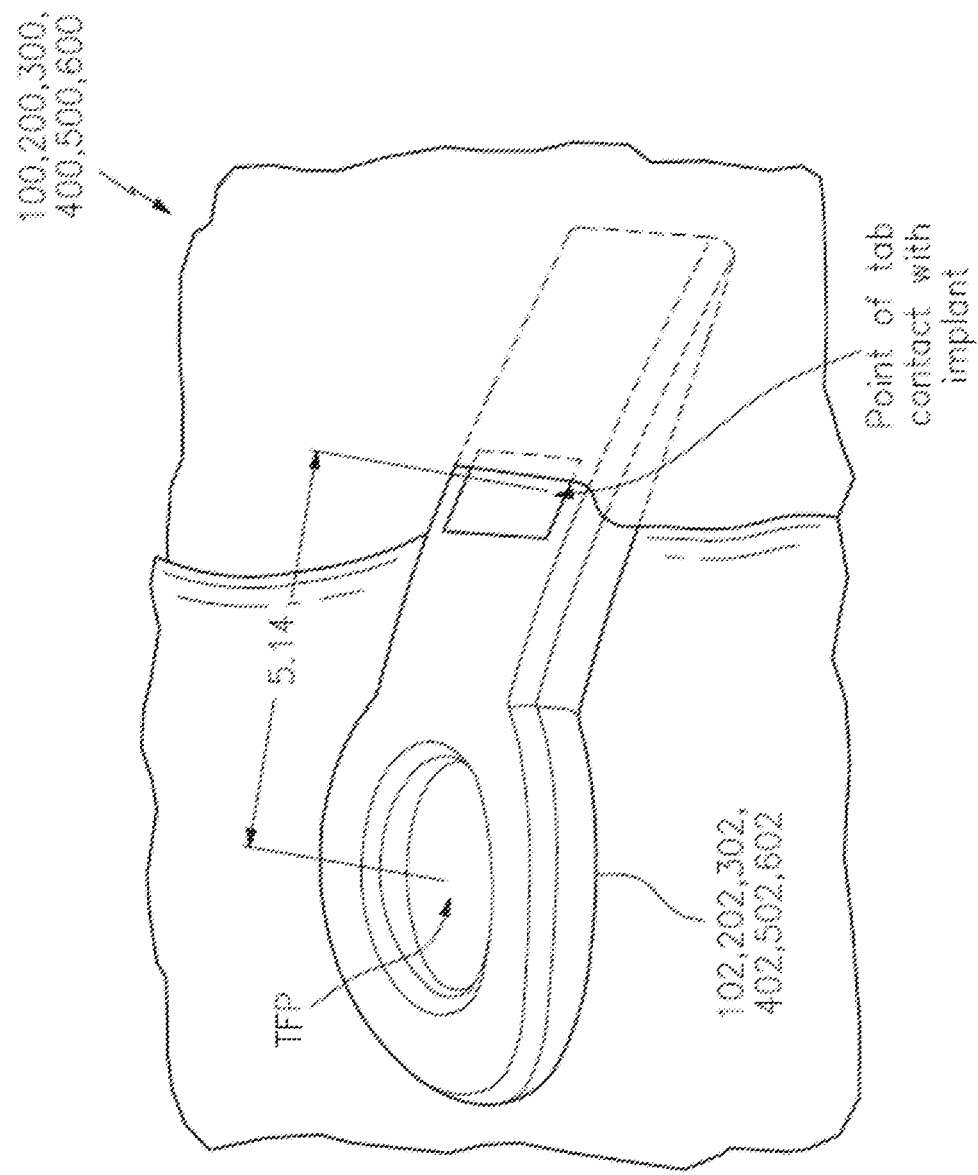
FIG. 9B is a side top down view of the cranial implant of FIG. 1 and the fixation tab of FIG. 7 associated with the skull of a patient.
Figure 10:
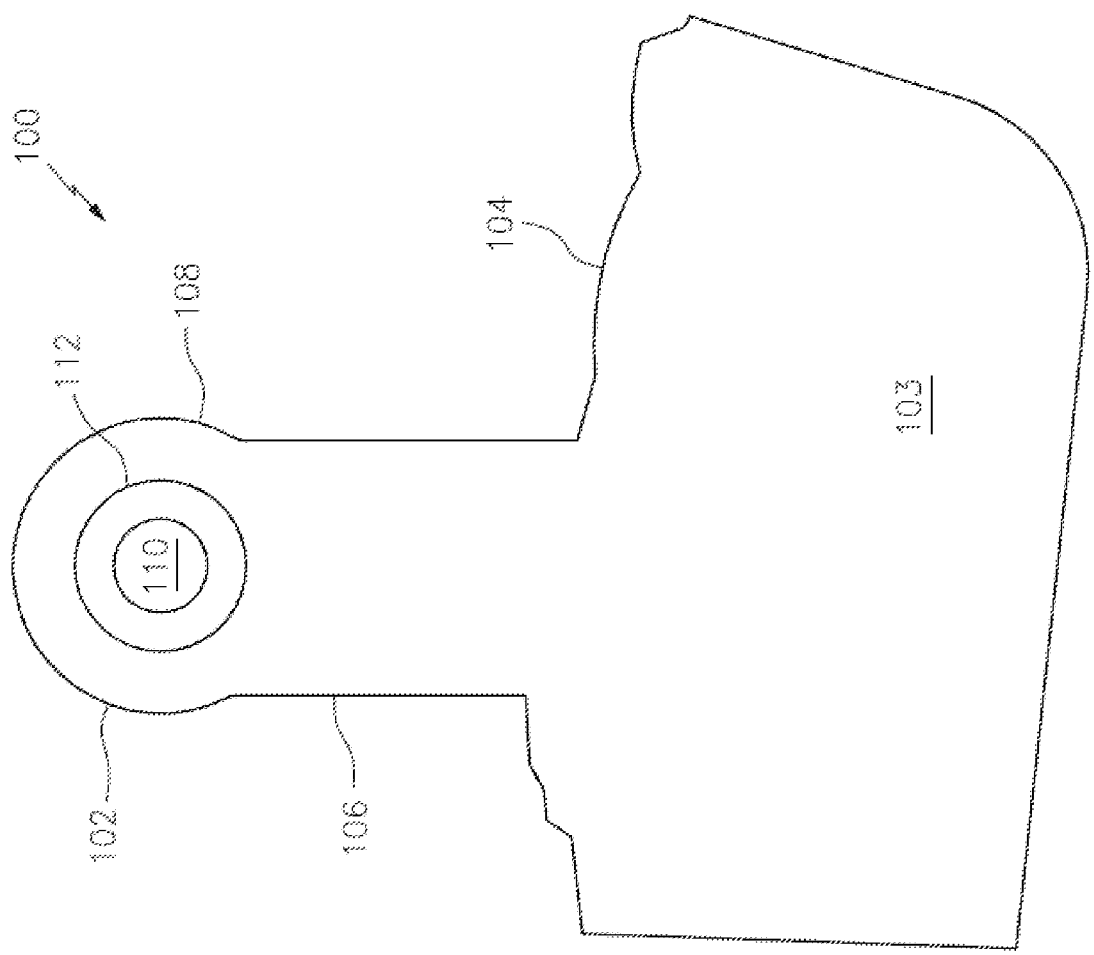
FIG. 10 is a top down illustrative view of the fixation tab of FIG. 7.

Referring to FIG. 9B, in one embodiment the focal point $T_{FP}$ may be located at the center of the anchor opening 110 and a spacing of approximately 5 mm to 7 mm exists between the tab focal point (i.e. center of opening 110) and the edge of the cranial implant 100. It should be appreciated that the $T_{FP}$ may should be configured and/or positioned in a manner such that the fixation tab 102 will sit flush with the skull bone to minimize bump and irregularities in the skull skin.

Figure 11:
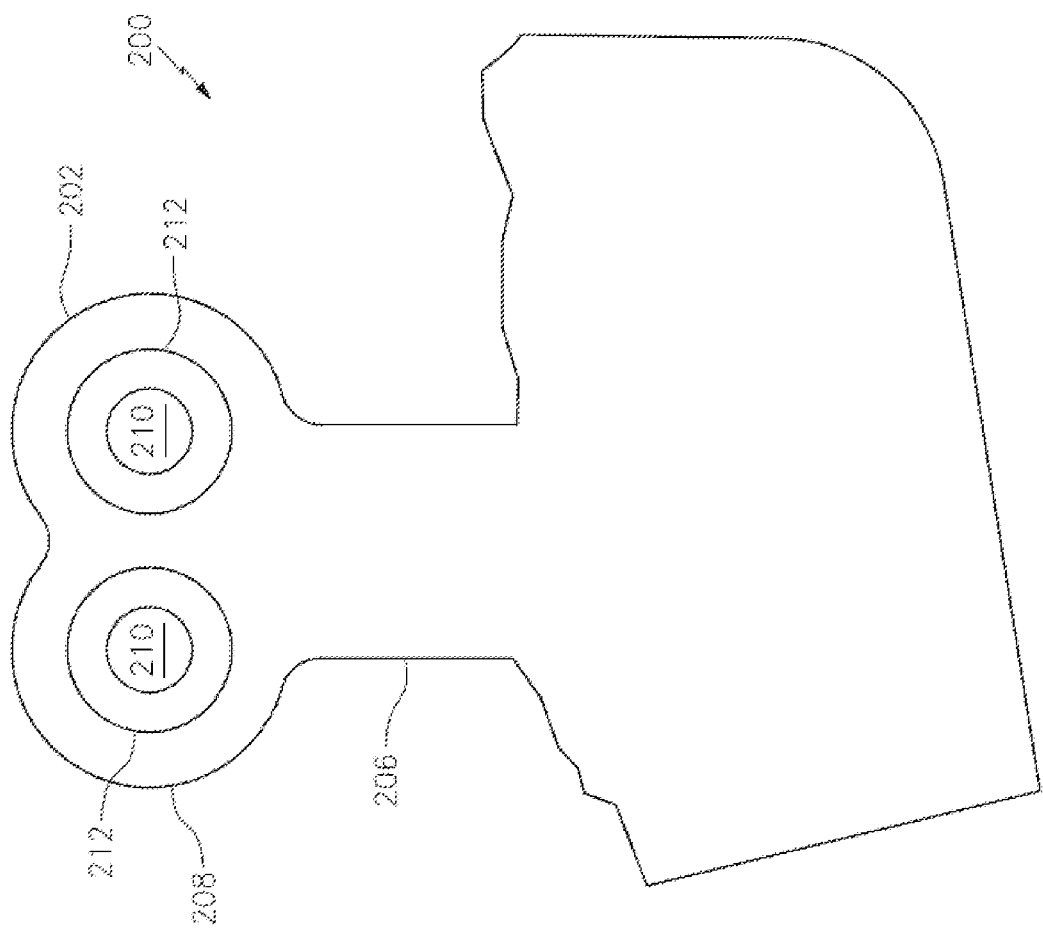
FIG. 11 is a top down illustrative view of a fixation tab, in accordance with a second embodiment of the invention.
Figure 12:
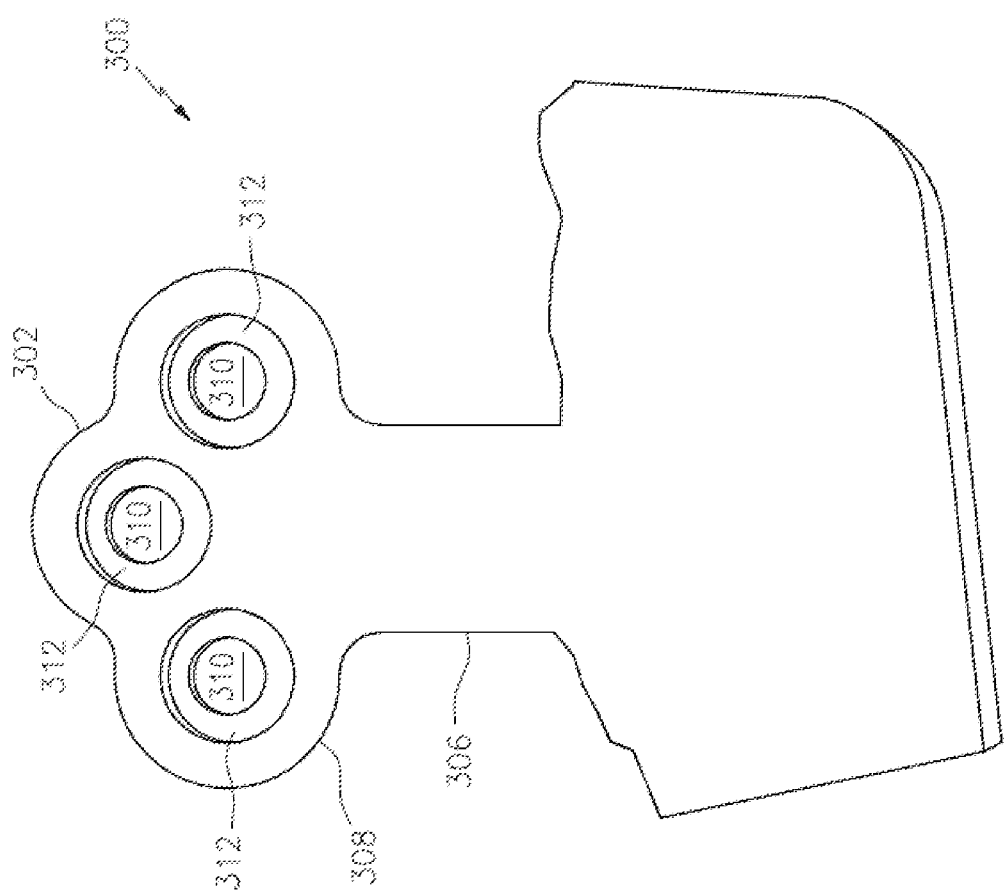
FIG. 12 is a top down illustrative view of a fixation tab, in accordance with a third embodiment of the invention.

Referring to FIG. 11, a cranial implant 200 having a fixation tab 202, in accordance with another embodiment of the invention is shown. In this embodiment, the fixation tab 202 includes a tab connecting shaft 206 and a tab anchoring end 208 having two anchor openings 210, wherein the tab anchoring end 208 includes two counter-sunk/counter-bore portions 212 (one around each anchor opening 210) that is counter-sunk/counter-bore into the tab anchoring end 208. Referring to FIG. 12, a cranial implant 300 having a fixation tab 302, in accordance with still yet another embodiment of the invention is shown. In this embodiment, the fixation tab 302 includes a tab connecting shaft 306 and a tab anchoring end 308 having three anchor openings 310, wherein the tab anchoring end 308 includes three counter-sunk/counter-bore portions 312 (one around each anchor opening 310) that is counter-sunk/counter-bore into the tab anchoring end 308.

Figure 13:
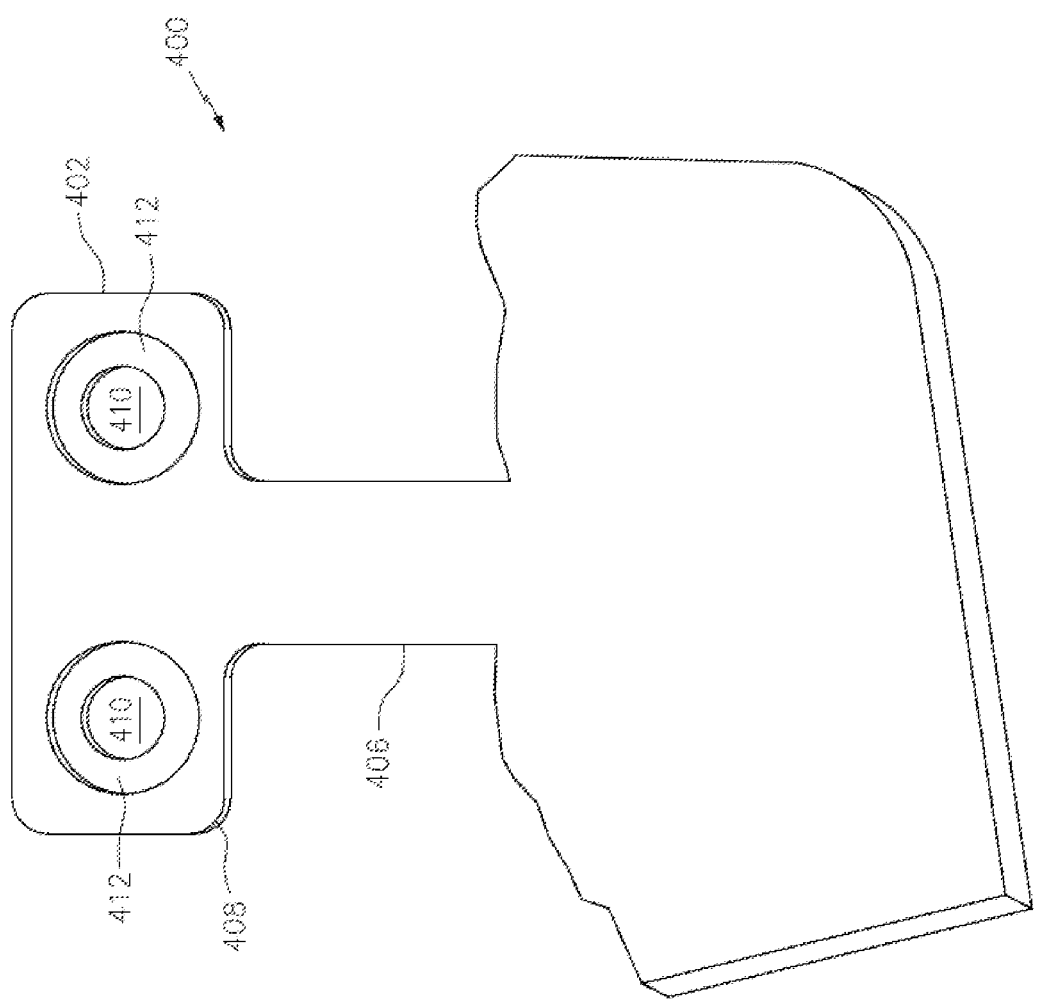
FIG. 13 is a top down illustrative view of a fixation tab, in accordance with a fourth embodiment of the invention.

Referring to FIG. 13, a cranial implant 400 having a fixation tab 402, in accordance with still yet another embodiment of the invention is shown. In this embodiment, the fixation tab 402 includes a tab connecting shaft 406 and a tab anchoring end 408 that is more rectangular in shape and has two (or at least one) anchor openings 410, wherein the tab anchoring end 408 includes two counter-sunk/counter-bore portions 412 (one around each anchor opening 410) that is counter-sunk/counter-bore into the tab anchoring end 408.

Figure 14:
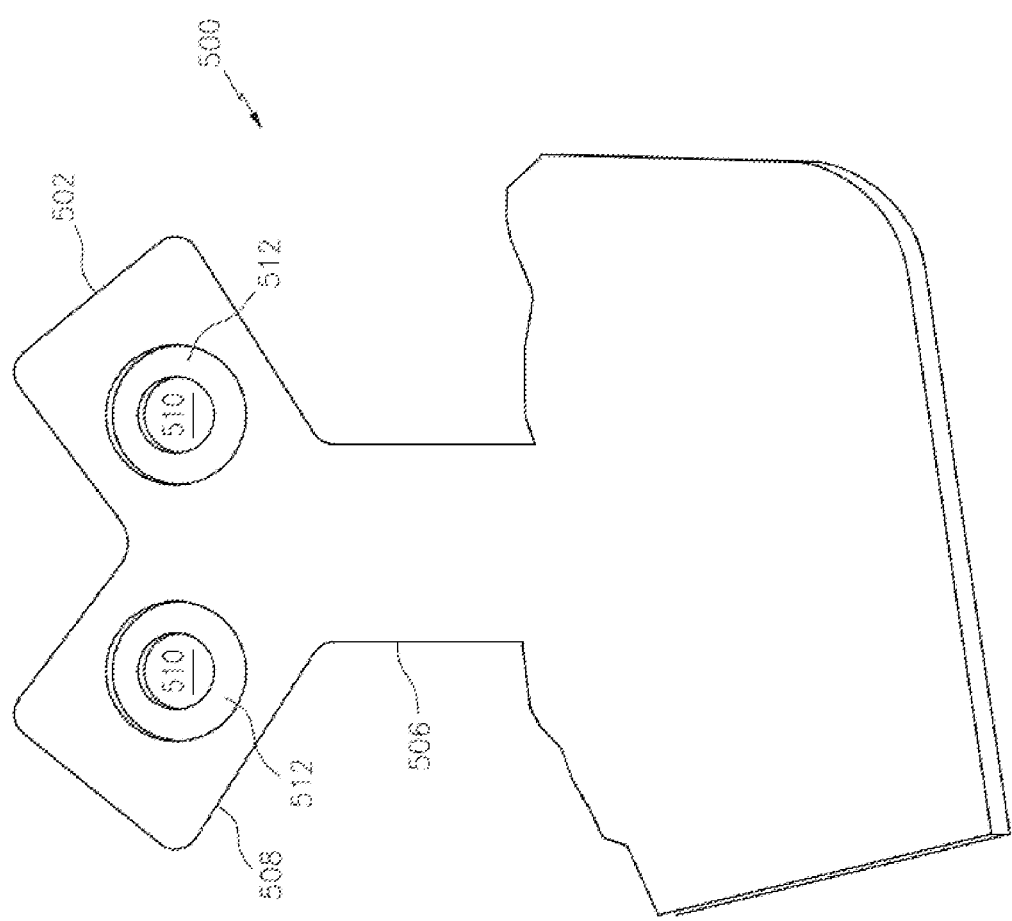
FIG. 14 is a top down illustrative view of a fixation tab, in accordance with a fifth embodiment of the invention.

Referring to FIG. 14, a cranial implant 500 having a fixation tab 502, in accordance with still yet another embodiment of the invention is shown. In this embodiment, the fixation tab 502 includes a tab connecting shaft 506 and a tab anchoring end 508 that is more triangular in shape and has two (or at least one) anchor openings 510, wherein the tab anchoring end 508 includes two counter-sunk/counter-bore portions 512 (one around each anchor opening 510) that is counter-sunk/counter-bore into the tab anchoring end 508.

Figure 15:
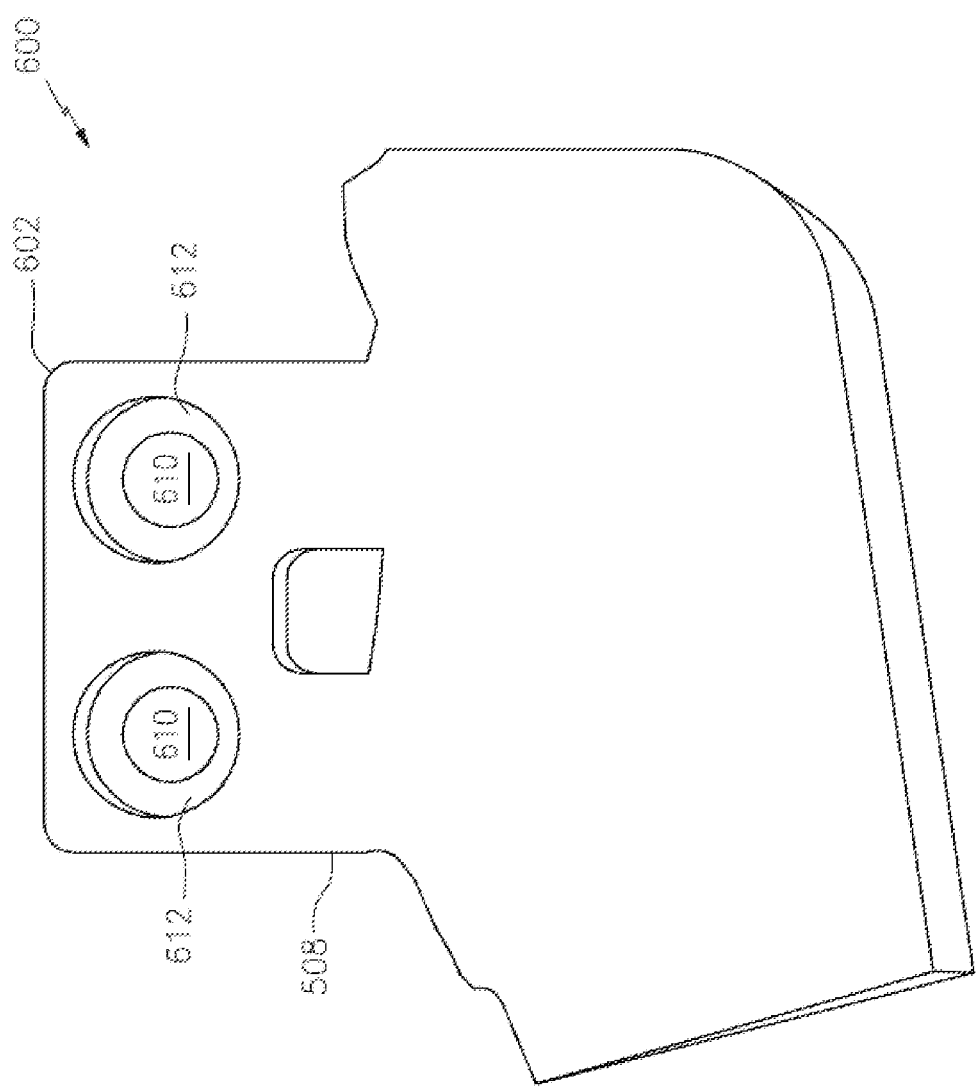
FIG. 15 is a top down illustrative view of a fixation tab, in accordance with a sixth embodiment of the invention.

Referring to FIG. 15, a cranial implant 600 having a fixation tab 602, in accordance with still yet another embodiment of the invention is shown. In this embodiment, the fixation tab 602 includes a tab anchoring end 608 that is more square in shape and has two (or at least one) anchor openings 610, wherein the tab anchoring end 608 includes two counter-sunk/counter-bore portions 612 (one around each anchor opening 610) that is counter-sunk/counter-bore into the tab anchoring end 608. It should be appreciated that in addition to the embodiments disclosed herein, fixation tabs having other shaped tab anchoring ends or tab connecting shafts may be used as desired.

Figure 16:
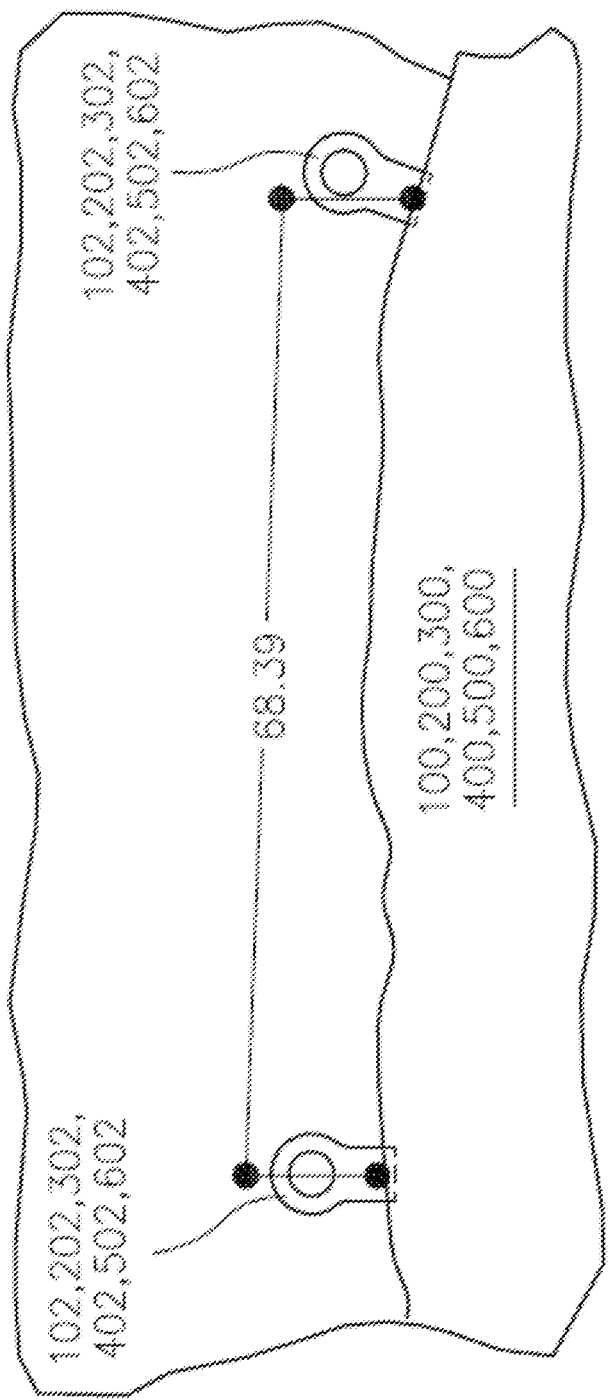
FIG. 16 is a top down view of a cranial implant and fixation tab having approximate spacing, in accordance with another embodiment of the invention.

It should be appreciated that the cranial implant 100, 200, 300, 400, 500, 600, 800 typically includes at least three (3) fixation tabs 102, 202, 302, 402, 502, 602, 802. However, it is contemplated that the cranial implant 100, 200, 300, 400, 500, 600, 800 may have any number of fixation tabs 102, 202, 302, 402, 502, 602, 802 as desired suitable to the desired end purpose. For example, referring to FIG. 16 in one embodiment a cranial implant 100, 200, 300, 400, 500, 600, 800 may include a plurality of fixation tabs 102, 202, 302, 402, 502, 602, 802 where each of the fixation tabs 102, 202, 302, 402, 502, 602, 802 is spaced apart from an adjacent fixation tab 102, 202, 302, 402, 502, 602, 802 by approximately 65 mm. Thus, an approximate 65 mm spacing exists between each tab measuring from the implant edge. In other words, a fixation tab 102, 202, 302, 402, 502, 602, 802 may be placed every 65 mm around the circumference of the cranial implant 100, 200, 300, 400, 500, 600, 800. It should be appreciated that typically (although not always) a fixation tab 102, 202, 302, 402, 502, 602, 802 may not be located in the temporal and/or orbital/facial region due to complications and aesthetic reasons. It should be appreciated that in other embodiments of the cranial implant 100, 200, 300, 400, 500, 600, 800 the fixation tabs 102, 202, 302, 402, 502, 602, 802 may be spaced apart from each other as desired.

Furthermore, it is contemplated that in other embodiments, the number of fixation tabs 102, 202, 302, 402, 502, 602, 802 used on a cranial implant 100, 200, 300, 400, 500, 600, 800 may be based on the circumference of the cranial implant 100, 200, 300, 400, 500, 600, 800. For example, the number of fixation tabs 102, 202, 302, 402, 502, 602, 802 may be responsive to how many fixation tabs 102, 202, 302, 402, 502, 602, 802 will fit the edge tabs 104, 204, 304, 404, 504, 604, 804 of the cranial implant 100, 200, 300, 400, 500, 600, 800.

Figure 17:
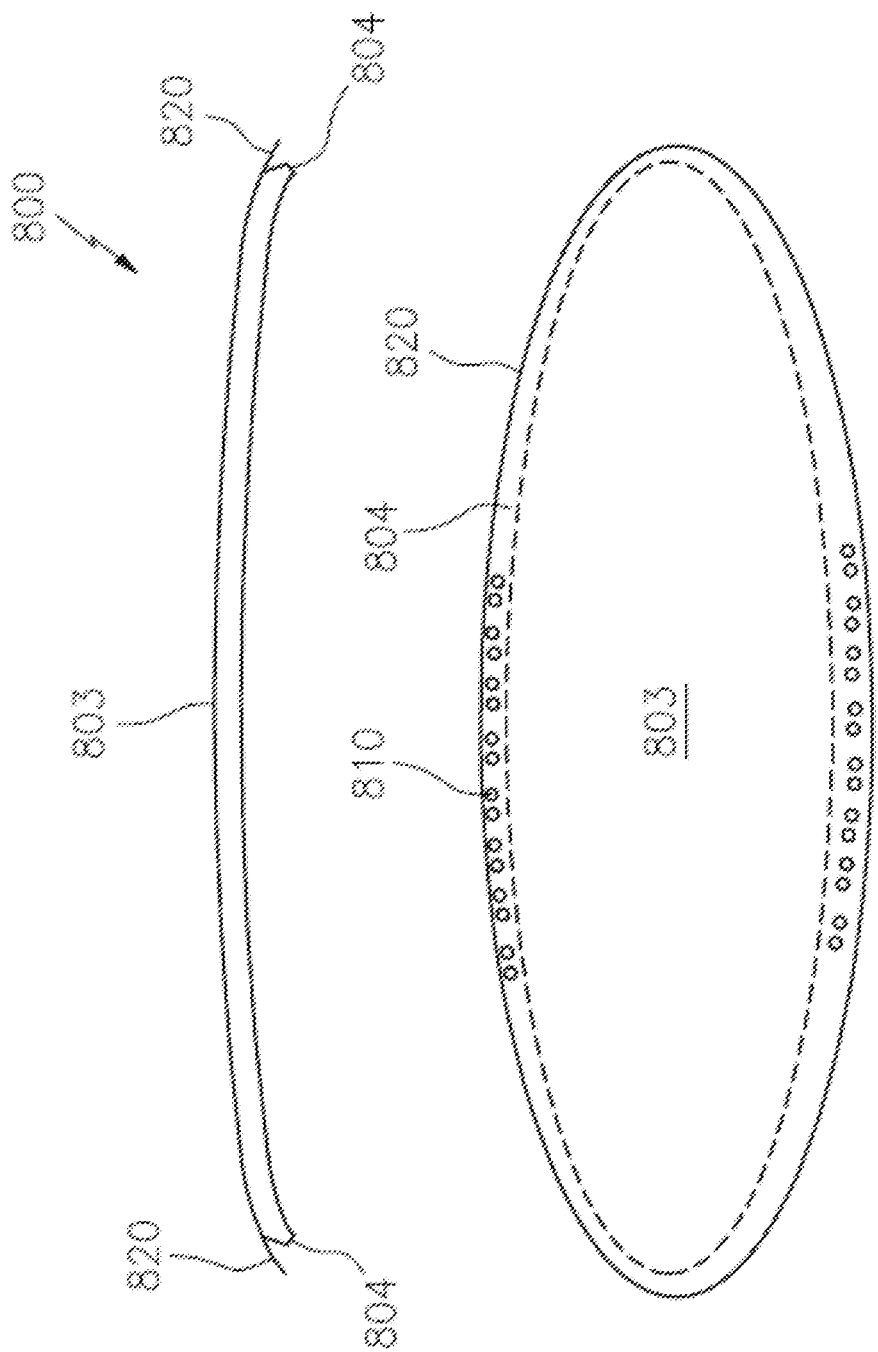
FIG. 17 is a side view and a top down view of a cranial implant having a lip that functions as a fixation tab, in accordance with still yet another embodiment of the invention.

Referring to FIG. 17, in still yet another embodiment it is contemplated that, in addition to, or in replace of, a fixation tab 802, a cranial implant 800 may include a lip portion 820 that extends out from the center portion 803 and along at least a portion of the edge 804 of the cranial implant 800. In this embodiment, the lip portion 820 may include anchor openings 810 for mounting the cranial implant 800 to the skull of a patient.

Figure 18:
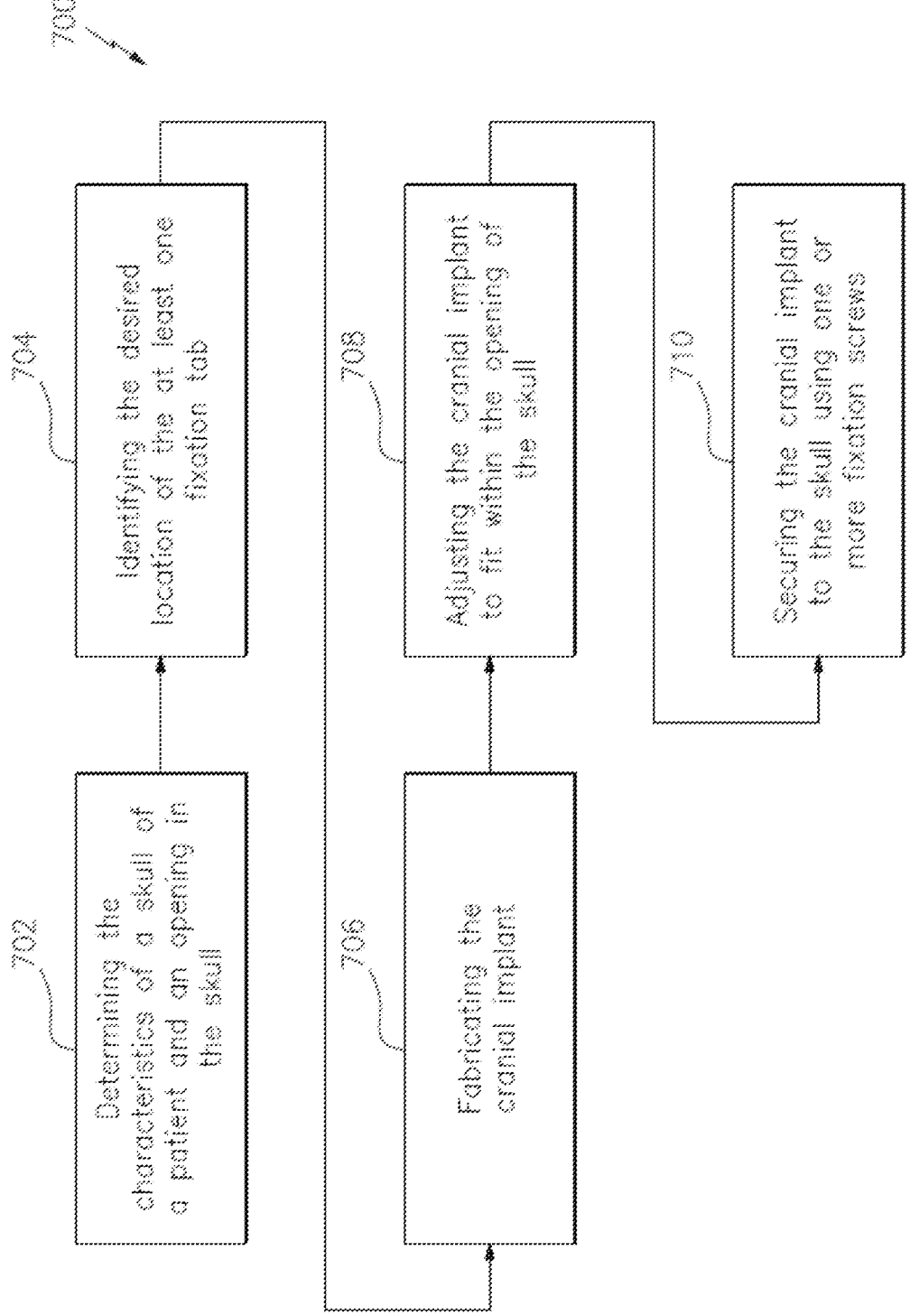
FIG. 18 is an operational block diagram illustrating a method for generating and implementing a cranial implant, in accordance with an embodiment of the invention.

Referring to FIG. 18, a method 700 for generating and implementing a cranial implant 100, 200, 300, 400, 500, 600 is provided in accordance with one embodiment of the invention and includes determining the characteristics of a skull of a patient and an opening in the skull, as shown in operational block 702. These characteristics may include, but are not limited to, the location of the opening, shape of the opening, shape of the skull (i.e. curvature) in the area of the opening and thickness of the skull in the area of the opening. Based on the characteristics of the skull and opening, the method 700 further includes determining where the fixation tabs 102, 202, 302, 402, 502, 602 will be located, as shown in operational block 704. This may be dependent on the location of the opening and the amount of skull surface area available to affix the fixation tabs 102, 202, 302, 402, 502, 602. The method further includes fabricating the cranial implant 100, 200, 300, 400, 500, 600, as shown in operational block 706. It should be appreciated that the cranial implant 100, 200, 300, 400, 500, 600 may be fabricated based on a predetermined algorithm and/or on the experience of the fabricator in response to at least one of the characteristic of the skull/opening and/or the determination of the location of the fixation tabs 102, 202, 302, 402, 502, 602. Additionally, although the cranial implant 100, 200, 300, 400, 500, 600 is preferably fabricated out of a polymeric biomaterial (such as Peek-Optima®), it should be appreciated that the cranial implant 100, 200, 300, 400, 500, 600 and/or fixation tabs 102, 202, 302, 402, 502, 602 may be constructed from any bio-compatible material suitable to the desired end purpose, such as ceramic, metal, plastic and/or any combination thereof. The fabricated cranial implant 100, 200, 300, 400, 500, 600 is then fitted into the opening of the skull such the cranial implant 100, 200, 300, 400, 500, 600 is flush (or as flush as possible) with the remainder of the skull, as shown in operational block 708. It should be appreciated that the surgeon may adjust the edges of the cranial implant 100, 200, 300, 400, 500, 600 to better fit within the skull opening. The cranial implant 100, 200, 300, 400, 500, 600 is then securely connected to the skull, as shown in operational block 710. This may be accomplished using fixation screws, wherein the fixation screws are located within the anchor openings 110, 210, 310, 410, 510, 610 of the fixation tabs 102, 202, 302, 402, 502, 602 and screwed into the skull.

It should be appreciated that the cranial implants 100, 200, 300, 400, 500, 600 each have anchor openings 110, 210, 310, 410, 510, 610 that include a counter-sunk/counter-bore portion 112, 212, 312, 412, 512, 612. It is contemplated that in other embodiments, the anchor openings 110, 210, 310, 410, 510, 610 may not have counter-sunk/counter-bore portions 112, 212, 312, 412, 512, 612.

It should be appreciated that the invention may be used with other types of implants (i.e. implants for other areas of the body) and thus is not limited to use with cranial implants. Moreover, additional information is provided in the attached appendix where the information does not and is not intended to limit the scope of the invention. Accordingly, all of the information contained herein may be combined together (individually or wholly) or taken singly to achieve varying embodiments of the invention and to add to the scope of the invention without limiting the invention to a particular embodiment.

Furthermore, in accordance with the present invention, the cranial implant 100, 200, 300, 400, 500, 600 and /or fixation tabs 102, 202, 302, 402, 502, 602 are preferably constructed from a polymeric biomaterial (such as Peek-Optima®). However, it should be appreciated that the cranial implant 100 and /or fixation tabs 102, 202, 302, 402, 502, 602 may be constructed from any bio-compatible material suitable to the desired end purpose, such as ceramic, metal, plastic and/or any combination thereof.

Moreover, while the invention has been described with reference to an exemplary embodiment, it will be understood by those skilled in the art that various changes, omissions and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

We claim:

1. A cranial implant for associating with the skull of a living body, wherein the skull includes a skull outer surface, the cranial implant comprising:
   an implant body configured to fit within a skull opening in the skull,
   wherein the skull includes a skull opening edge which defines the skull opening, and
   wherein the implant body includes an implant body top surface and an implant body edge, wherein, when the implant body edge is pre-fabricated and pre-shaped responsive to the skull opening edge, wherein when the implant body is located within the skull opening,
   the implant body edge is located adjacent the skull opening edge to be in contact with the skull opening edge, and
   the implant body top surface is substantially flush with the skull outer surface such that the transition between the skull outer surface and the implant body top surface is substantially smooth; and
   at least one fixation tab for anchoring the implant body to the skull, wherein the at least one fixation tab is integral with the implant body, and includes a tab connecting shaft and a tab anchoring end, wherein the tab anchoring end includes at least one anchor opening, wherein the at least one fixation tab is pre-shaped to approximate the shape of the skull.

2. The cranial implant of claim 1, wherein the at least one fixation tab is integrally connected to the cranial implant.

3. The cranial implant of claim 1, wherein the at least one fixation tab is located proximate the implant body edge.

4. The cranial implant of claim 1, wherein a counter-sunk/counter-bore portion is proximate the at least one anchor opening to surround at least a portion of the at least one anchor opening.

5. The cranial implant of claim 1, wherein the at least one fixation tab includes three fixation tabs.

6. The cranial implant of claim 1, wherein the cranial implant includes an implant surface area and wherein the number of fixation tabs is responsive to the circumference of the implant body edge.

7. A method for generating and implementing a cranial implant, wherein the cranial implant includes at least one fixation tab, the method comprising:
   determining the characteristics of a skull of a patient and an opening in the skull;
   identifying the desired location of the at least one fixation tab;
   fabricating the cranial implant based on at least one of a predetermined algorithm and experience of a fabricator in response to at least one of the characteristic of the skull/opening in the skull and the location of the fixation tabs:
   adjusting the cranial implant to fit within the opening of the skull such the cranial implant is substantially flush with a surface of the skull; and
   securing the cranial implant to the skull using one or more fixation screws.

8. The cranial implant of claim 1, wherein the implant body is constructed from a bio-compatible material and is at least one of a ceramic material, a plastic material, a composite material or any combination thereof.

9. The cranial implant of claim 1, wherein the implant body and at least one fixation tab are made from a polymeric bio-compatible material.

10. The cranial implant of claim 9, wherein the implant body and at least one fixation tab are made from PEEK (polyether ether ketone).

11. The cranial implant of claim 1, wherein the at least one anchor opening includes a counter-sunk/counter-bore portion.

12. The cranial implant of claim 1, wherein the at least one fixation tab includes a tab focus point located between the tab connecting shaft and the tab anchoring end, and wherein the at least one fixation tab is curved between 3 and 20 degrees about the tab focus point.

* * * * *